United States Patent [19]

Reichl

[11] Patent Number: 4,534,772

[45] Date of Patent: Aug. 13, 1985

[54] PROCESS OF ETHER SYNTHESIS

[75] Inventor: Eric H. Reichl, Greenwich, Conn.

[73] Assignee: Conoco Inc., Wilmington, Del.

[21] Appl. No.: 546,233

[22] Filed: Oct. 28, 1983

Related U.S. Application Data

[63] Continuation-in-part of Ser. No. 372,507, Apr. 28, 1982, abandoned.

[51] Int. Cl.$^3$ .......................... C10L 1/02; C10L 1/18
[52] U.S. Cl. ........................................ 44/53; 518/702; 518/703; 568/697; 585/639; 44/56; 44/77
[58] Field of Search ................ 518/702, 703; 568/697; 585/639; 44/53, 56, 77

[56] References Cited

U.S. PATENT DOCUMENTS

| | | |
|---|---|---|
| 1,423,049 | 7/1922 | Tunison . |
| 2,067,385 | 1/1937 | Evans et al. . |
| 3,342,879 | 9/1967 | Pine . |
| 3,821,315 | 6/1974 | Massie et al. . |
| 3,920,717 | 11/1975 | Marion . |
| 4,175,210 | 11/1979 | Selwitz et al. . |
| 4,231,756 | 11/1980 | King . |
| 4,299,998 | 11/1981 | Stapp . |

FOREIGN PATENT DOCUMENTS

| | | |
|---|---|---|
| 50-41803 | 4/1975 | Japan . |
| 247177 | 4/1927 | United Kingdom . |

OTHER PUBLICATIONS

Suntech Inc., The Potential of MTBE from Coal, Nov. 11-13, 1980, Dearborn, Michigan, pp. 1-24.

*Primary Examiner*—Howard T. Mars
*Attorney, Agent, or Firm*—William A. Mikesell, Jr.

[57] ABSTRACT

A method for producing fuel comprised of gasoline rich in methanol and methyl ethers derived from coal, which process comprises gasifying the coal to produce carbon monoxide and hydrogen, steam shifting the gasification product to produce additional hydrogen, cleaning up the shifted product, catalytically converting the cleaned shifted gas to a mixture of alcohols, separating a methanol fraction from the mixture of alcohols, dehydrating the remaining alcohols to olefins, etherifying the olefin mixture with a portion of the removed methanol fraction, and blending into gasoline the resulting ether mixture and a second portion of the removed methanol fraction.

2 Claims, 1 Drawing Figure

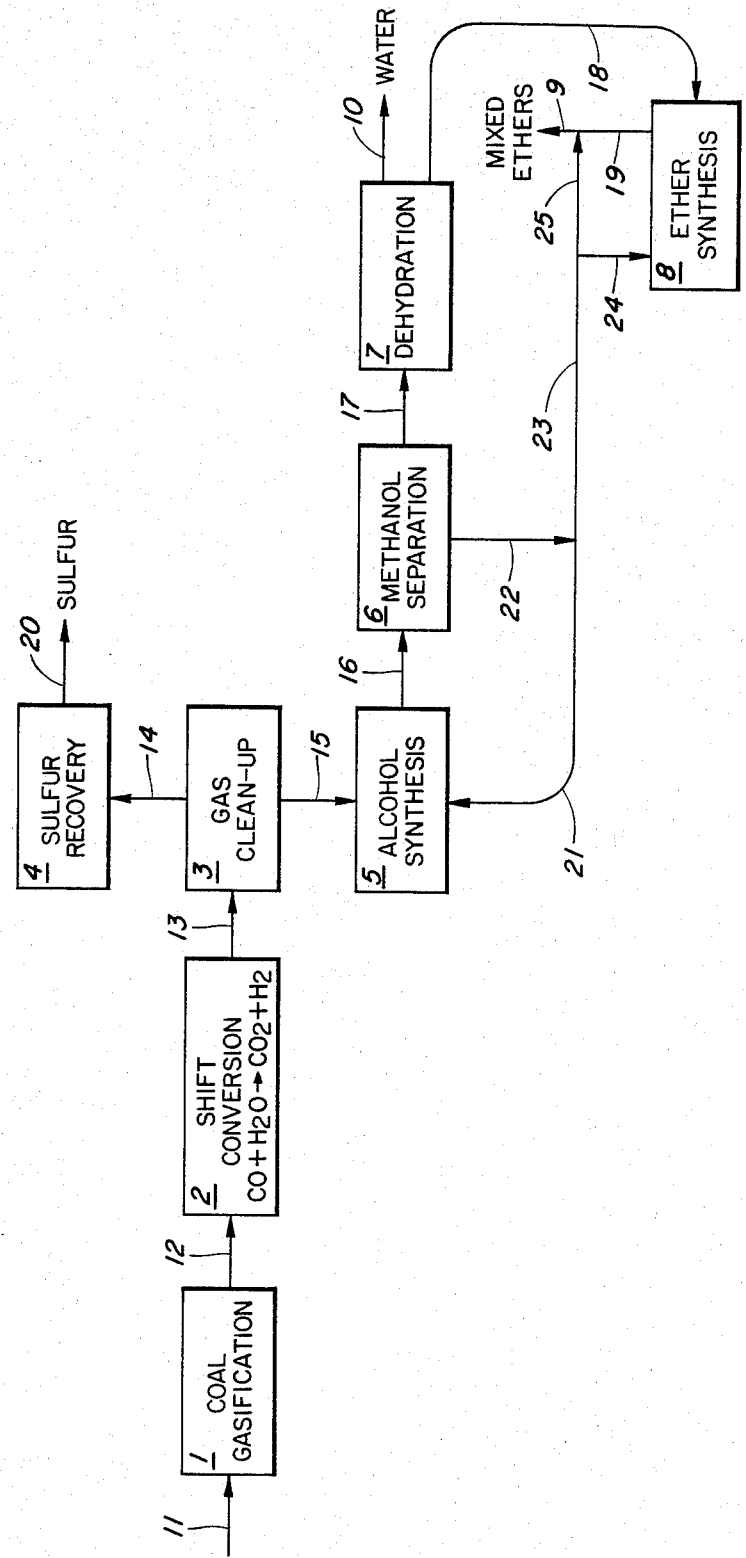

PROCESS OF ETHER SYNTHESIS

BACKGROUND OF THE INVENTION

This is a continuation-in-part of U.S. Ser. No. 372,507 filed Apr. 28, 1982.

Suntech, U.S. Department of Energy, Highway Vehicle Systems Contractors Coordination Meeting, Nov. 11-13, 1980, Dearborn, Mich. discloses a method of making isobutyl ethers from coal. The process includes the gasification of the coal followed by shift conversion gas clean-up alcohol synthesis methanol separation isobutanol separation isobutanol dehydration and esterification with methanol.

Evans et al in U.S. Pat. No. 2,067,385 discloses a process for making ethers from natural gas as by cracking or from gases derived from coal. The process includes reacting a secondary base olefin with an aliphatic alcohol in the presence of a non-basic acting condensing agent which promotes the condensation action between the olefin and the alcohol.

Massie et al U.S. Pat. No. 3,821,315 discloses symmetrical and non-symmetrical ethers prepared by the addition of alcohols to olefins in the presence of a catalyst comprising an organomolybdenum compound.

Selwitz et al U.S. Pat. No. 4,175,210 discloses a process for converting an olefin or mixture of olefins to an ether or a mixture of ethers which comprises reacting the olefin or mixture of olefins with an alcohol in contact with a silicatungstic acid.

Woods et al in U.S. Pat. No. 4,204,077 discloses a process for making olefinic hydrocarbon mixtures containing isobutylene and isoamylene which are etherified with methanol to obtain higher octane compounds.

Lien U.S. Pat. No. 2,399,126 discloses the manufacture of ethers from alcohols and olefins in the presence of an improved catalyst. The feed may consist of a pure olefin such as ethylene, propylene, butylene, or higher olefin with a pure alcohol such as methyl, ethyl, propyl, butyl or higher alcohol. Where the process is employed to make solvents in which chemical purity is not necessary, mixtures of different alcohols and olefins may be employed.

Patart U.K. Patent specification No. 247,177 discloses a process of catalytic reduction of carbon monoxide under pressure which permits direct reaction in the formation of alcohols having a higher molecular weight than methanol.

King in U.S. Pat. No. 4,231,756 discloses a gasoline and petroleum fuel supplement formed of a combination of ingredients including methanol xylene, ethyl alcohol and at least one alkali methal hydroxide.

BRIEF DESCRIPTION OF THE DRAWING

The drawing is a schematic presentation of the ether formation in accordance with the present invention.

SUMMARY OF THE INVENTION

A process for producing a high octane liquid gasoline fuel product mixture rich in methanol and methyl ethers from coal consisting of the sequence of steps as follows:
(a) gasifying coal to form a coal gasification product gas mixture comprising hydrogen and carbon monoxide,
(b) contacting the coal gasification product gas with water and a shift conversion catalyst means to catalytically react the water with the carbon monoxide of the gasification product gas to form a shift product gas mixture comprising carbon dioxide and hydrogen,
(c) contacting the shift product gas mixture with an alcohol synthesis catalyst means to form a synthesis product mixture of alcohols, the synthesis product mixture of alcohols comprising methanol, the alcohol synthesis catalyst means comprising a fixed bed of alkali modified zinc oxide and chromium oxide,
(d) separating the synthesis product mixture of alcohols into a methyl alcohol separation product mixture and a higher alcohol separation product mixture, the methyl alcohol separation product mixture comprising a substantially larger proportion of methanol than the synthesis product mixture of alcohols, the higher alcohol separation product mixture further comprising substantially all of the alcohols other than methanol from the synthesis product mixture of alcohols,
(e) dehydrating the higher alcohol separation product mixture with a catalytic dehydration means to form a dehydration product mixture and water, the dehydration product mixture comprising olefins, the catalytic dehydration means comprising alumina,
(f) catalytically reacting the olefins of the dehydration product mixture with a portion of the methyl alcohol separation product mixture in the presence of an ether synthesis catalyst means at about 125° F. and 300 psig to form a methyl ether product mixture, the ether synthesis catalyst means comprising acidic ion exchange resin,
(g) mixing the remainder of the methyl alcohol separation product with the methyl ether product mixture to form a methyl alcohol and methyl ether product mixture as substantially the only liquid product of the coal gasified in step (a),
(h) mixing gasoline with the methyl alcohol and methyl ether product mixture to form a high octane fuel product whereby substantially all of the alcohols formed in step (c) are formed into a mixture of methyl alcohol and methyl ethers which is then mixed with gasoline to produce a high octane liquid gasoline fuel product rich in methyl alcohol and methyl ethers.

The process of the present invention beneficially provides an improved and simplified process for the production of ethers suitable for use in blending high octane gasoline from coal.

Beneficially a liquid fuel additive product mixture of methanol and methyl ethers is formed from coal. The process provides for novel, cost effective, simplified production of the fuel additive.

DETAILED DESCRIPTION OF THE INVENTION

With more particular reference to the drawing, the schematic presented shows an ether synthesis in accordance with the present invention. Coal is fed through line 11 to the coal gasification section 1. Syn gas formed in the coal gasification section 1 passes through line 12 to the shift conversion section 2. The syn gas in line 12 comprises hydrogen, carbon monoxide, carbon dioxide and hydrogen sulfide. In the shift conversion section 2 carbon monoxide and water are catalytically reacted to form hydrogen and carbon dioxide. A hydrogen enriched syn gas mixture passes from the shift conversion section 2 through line 13 into the gas clean-up section 3. The gas clean-up section 3 may be a scrubber. Hydrogen sulfide and carbon dioxide are scrubbed from the syn gas in the clean-up section 3 and passed through line 14 to the sulfur recovery section 4. A sulfur product passes through line 20 from the sulfur recovery section 4. The clean syn gas passes through line 15 into the alcohol synthesis section 5. The alcohol synthesis section 5 converts the syn gas into a mixture of alcohols. Within the alcohol synthesis section 5 is a catalyst at alcohol forming conditions. Exemplary of suitable catalyst would be a fixed bed of alkali modified zinc oxide and chromium oxide $ZnO/Cr_2O_3$ catalyst at elevated temperature pressure. The mixture of alcohols passes through line 16 to the methanol separation section 6. The methanol separation section may for example be distillation at low temperatures. The alcohol mixture with a reduced methanol concentration passes through line 17 to the dehydration section 7. The dehydration section 7 catalytically dehydrates the alcohols in the alcohol mixture to a mixture of the corresponding olefins. Exemplary of suitable catalysts for use as the catalytic material of dehydration is alumina. Water is removed from the dehydration section 7 through line 10. The olefins formed in the dehydration section 7 pass through line 18 to the ether synthesis section 8. Methanol through line 24 passes into the ether synthesis section 8. The methanol and mixture of olefins are catalytically reacted to form the corresponding methyl ethers. Suitable conditions for the formation of the methyl ethers would be temperatures of about 125° F. and pressure of about 300 psig in the presence of an acidic ion exchange resin.

Methanol from the methanol separation section 6 passes through line 22 from which a portion passes through line 21 to be recycled to the methanol synthesis section 5. An additional portion of the methanol from the methanol separation section 6 passes through line 22 into line 23 from which it passes in controllable amounts to the ether synthesis section 8 through line 24 or for combination with the mixed ethers through line 25. The mixed ethers from the ether synthesis section 8 pass through line 19 and mix with methanol from line 25 as it passes into line 9.

The mixed ethers produced by the process of the present invention may be beneficially mixed with gasoline to produce higher octane fuel.

EXAMPLE 1000 pounds of bituminous coal is gasified with water to form a gaseous mixture including CO, $H_2$ and $H_2S$. A portion of the CO of the mixture is water gas shifted in the presence of shift catalyst to form $CO_2$ and $H_2$. The $H_2S$ is then scrubbed from the mixture.

The mixture of $H_2$, CO and $CO_2$ is then passed through a $ZnO/Cr_2O_3$ catalyst with 1% alkali at about 765° F. and 4000 psig to form on a weight percentage basis:

|  |  |  |
|---|---|---|
| methanol | 50% |  |
| dimethyl ether | 2.5% |  |
| ethanol | 1% |  |
| propanol | 2% |  |
| isobutanol | 13% |  |
| amyl alcohol | 2% |  |
| $C_6$-$C_7$ alcohol | 2.5% |  |
| higher alcohols | 2% |  |
| water | 25% |  |

Methanol is distilled from the mixture leaving the aqueous alcohol-ether mixture. The alcohol-ether mixture is distilled from the water, condensed and passed through an alumina dehydration catalyst. The olefins formed are mixed with methanol in a 1:1 molar ratio and passed through an acidic ion exchange resin ether synthesis catalyst at about 125° F. and 300 psig to form on a weight percentage basis:

|  |  |
|---|---|
| dimethyl ether | 10% |
| methyl ethyl ether | 4% |
| methyl propyl ether | 8% |
| methyl isobutyl ether | 52% |
| methyl amyl ether | 8% |
| higher methyl ethers | 18% |

The methyl ether mixture is mixed with an equal weight of methanol to form a fuel additive mixture. The fuel additive mixture is added to gasoline in a ratio of 1:10 (additive to gasoline) on a weight basis to form a supplemental fuel mixture. The supplemental fuel mixture is combusted in an internal combustion engine to power an automobile.

Having thus described the invention by reference to certain of its preferred embodiments it is respectfully pointed out that embodiments described are illustrative rather than limiting in nature and that many variations and modifications are possible within the scope of the present invention. Such variations and modifications may appear obvious and desirable to those skilled in the art upon a review of the foregoing description of preferred embodiments.

Having thus described the invention, I claim:

1. A process for producing a high octane liquid gasoline fuel product mixture rich in methanol and methyl ethers from coal consisting of the sequence of steps as follows:
    (a) gasifying coal to form a coal gasification product gas mixture comprising hydrogen and carbon monoxide,
    (b) contacting said coal gasification product gas with water and a shift conversion catalyst to catalytically react said water with said carbon monoxide of said gasification product gas to form a shift product gas mixture comprising carbon dioxide and hydrogen,
    (c) subjecting said shift product gas mixture to a clean-up step to produce a cleaned shift product gas mixture,
    (d) contacting said cleaned shift product gas mixture with an alcohol synthesis catalyst to form a synthesis product mixture of alcohols, said synthesis product mixture of alcohols comprising methanol, and said alcohol synthesis catalyst comprising alkali modified zinc oxide and chromium oxide,
    (e) separating said synthesis product mixture of alcohols into a methyl alcohol separation product mixture and a higher alcohol separation product mixture, said methyl alcohol separation product mixture comprising a substantially larger proportion of methanol than said synthesis product mixture of alcohols, and said higher alcohol separation product mixture further comprising substantially all of the alcohols other than methanol from said synthesis product mixture of alcohols,
    (f) dehydrating said higher alcohol separation product mixture with a catalyst to form a dehydration product mixture and water, said dehydration product mixture comprising olefins, and said catalyst comprising alumina,
    (g) catalytically reacting said olefins of said dehydration product mixture with a portion of said methyl alcohol separation product mixture in the presence of an ether synthesis catalyst at about 125° F. and 300 psig to form a methyl ether product mixture, said ether synthesis catalyst comprising acidic ion exchange resin, (h) mixing the remainder of said methyl alcohol separation product with said methyl ether product mixture to form a methyl alcohol and methyl ether product mixture as substantially the only liquid product of said coal gasified in step (a), and (i) mixing gasoline with said methyl alcohol and methyl ether product mixture to form a high octane fuel product, whereby substantially all of the alcohols formed in step (d) are formed into a mixture of methyl alcohol and methyl ethers and are mixed with gasoline to produce a high octane liquid gasoline fuel product rich in methyl alcohol and methyl ethers.

2. The process of claim 1 wherein said clean-up step comprises scrubbing.

* * * * *